(12) United States Patent
Chia et al.

(10) Patent No.: US 6,259,941 B1
(45) Date of Patent: *Jul. 10, 2001

(54) INTRAVASCULAR ULTRASOUND LOCATING SYSTEM

(75) Inventors: Weng-Kwen Raymond Chia, Irvine; Hosheng Tu, Tustin, both of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/275,553

(22) Filed: Mar. 24, 1999

Related U.S. Application Data

(63) Continuation-in-part of application No. 08/954,001, filed on Oct. 20, 1997, now Pat. No. 5,954,649.

(51) Int. Cl.[7] ....................................................... A61B 5/05
(52) U.S. Cl. ............................................ 600/424; 607/122
(58) Field of Search ................................... 600/424, 407, 600/437, 373; 607/122

(56) References Cited

U.S. PATENT DOCUMENTS

| 5,480,422 | * | 1/1996 | Ben-Haim | 607/122 |
| 5,722,402 | * | 3/1998 | Swanson et al. | 607/122 |
| 5,735,280 | * | 4/1998 | Sherman et al. | 601/2 |
| 5,840,031 | * | 11/1998 | Crowley | 607/122 |
| 5,868,673 | * | 2/1999 | Vesely | 600/407 |
| 5,954,649 | * | 9/1999 | Chia et al. | 600/424 |

* cited by examiner

Primary Examiner—Brian L. Casler

(57) ABSTRACT

An improved catheter system having intravascular ultrasound locating capabilities comprising a locator catheter and an ultrasound receiver catheter resulting in an effective electrophysiology procedure without undesired side effects of using a conventional x-ray imaging system. Said catheter system comprising a locator catheter, a reference catheter and a data acquisition computer; the locator catheter comprises at least one electrode at its distal tip section and an ultrasound crystal secured on the catheter shaft proximal to the distal end. The reference catheter comprises at least three ultrasound crystal beacons, a first ultrasound crystal beacon of said at least three ultrasound crystal beacons being located at the distal end of the reference catheter and being spaced apart from the remaining ultrasound crystal beacons, wherein the first ultrasound crystal beacon is adapted to be inserted into a vascular vessel, the reference catheter having pre-determined locations with reference to an external locating calibration system, wherein said ultrasound beacons can emit and receive ultrasound signals.

19 Claims, 5 Drawing Sheets

US 6,259,941 B1

INTRAVASCULAR ULTRASOUND LOCATING SYSTEM

CROSS-REFERENCE TO RELATED APPLICATIONS

This application is a continuation-in-part of application Ser. No. 08/954,001, filed on Oct. 20, 1997 now U.S. Pat. No. 5,954,649.

FIELD OF THE INVENTION

The present invention generally relates to improved constructions for a catheter system. More particularly, this invention relates to catheters and methods for mapping cardiac arrhythmias and ablating cardiac tissues via a steerable catheter system having intravascular ultrasound locating capabilities, comprising a locator catheter and a reference catheter that is capable of being placed intravascually, resulting in an effective electrophysiology procedure without undesired side effects of using a conventional x-ray imaging system.

BACKGROUND OF THE INVENTION

Symptoms of abnormal heart rhythms are generally referred to as cardiac arrhythmias, with an abnormally rapid rhythm being referred to as tachycardia. The present invention is concerned with the treatment of tachycardias that are frequently caused by the presence of an "arrhythmogenic site" or "accessory atrioventricular pathway" close to the inner surface of the chambers of a heart. The heart includes a number of normal pathways that are responsible for the propagation of electrical signals from the upper to the lower chambers necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the electrode or transducer to the cardiac tissue in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms. In the paroxysmal AFib, the origin of the arrhythmia may lie near the ostium of or inside a pulmonary vein. A complete circular lesion is required around the ostium or the wall of the pulmonary vein to cure the arrhythmia. It is imperative to have an accurate locating system.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area. For paroxysmal AFib indications, a catheter is approached from the atrium to the ostium of a pulmonary vein. The tip section of a locator catheter is referred to here as the portion of that catheter shaft containing the electrode means which may be deflectable and may be adapted to form a circular or an irregular-shape complete loop lesion. The electrode means is to be positioned against the ostium of the pulmonary vein or inside the vein, whereby the circular electrode means having a firm wire or coil electrode for circular lesion ablation.

The mapping and ablation procedures require means to locate the catheter; especially the tip section of said catheter, to the exact site of the arrhythmogenic sources. In the case of paroxysmal AFib, the location is about the pulmonary veins. The conventional method uses x-ray fluoroscope to image the location of the catheter. While x-ray imaging is quite successful, some patients, such as the pregnant women, the fluoro-phobic patients and the like, can tolerate little x-ray exposure. It is imperative that other imaging means be used to locate the catheter within the body of a patient.

Ultrasound imaging has been used extensively to reveal the existence of a device having the ultrasound emitter. In the U.S. Pat. No. 4,794,931, there has been disclosed a catheter and system which can be utilized for ultrasonic imaging. However, there is no disclosure on the technique of using ultrasound-locating means to generate the three-dimensional location data intravascularly. Based on recent advances in computer data analysis capability, the speed of analyzing the data obtained from a 3-D ultrasound locating system becomes feasible.

While an electrophysiology mapping and/or ablation procedure using an existing catheter has had promising results under x-ray imaging, reduction or elimination of x-ray exposure becomes a clinical need and a health issue to certain types of patients undergoing the catheter-based treatment. Therefore there is a need for an improved catheter system having intravascular ultrasound locating capabilities.

SUMMARY OF THE INVENTION

In general, it is an object of the present invention to provide an improved catheter system for positioning the mapping and/or ablation catheter. It is another object of the present invention to provide a catheter system having the capability to generate three-dimensional location coordinates for the mapping and/or ablation catheter. It is still another object of the present invention to provide a catheter system using the ultrasound locating technique. It is another object of the present invention to provide a catheter system with ultrasound receiving means inserted in the body intravascularly of a patient for three-dimensional locating capabilities. It is another object of the present invention to provide a catheter system with ultrasound receiving means external of the body of a patient for three-dimensional locating capabilities.

It is still another object of the present invention to provide a catheter system comprising a locator catheter and a reference receiver catheter, wherein a plurality of ultrasound crystals are secured on said catheters having emitting and receiving ultrasonic signals capabilities. In one embodiment, at least one ultrasound crystal is secured on the locator catheter and at least three crystals are secured on the reference catheter. To further identify and calibrate the location of the locator catheter, at least four crystals are secured on the reference catheter in an alternate embodiment.

In a preferred embodiment, a catheter system comprises a locator catheter, a reference catheter and a data acquisition computer system, the locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end for transmitting ultrasound signals; a connector secured to the proximal end of said handle. The reference catheter comprises at least three ultrasound crystal beacons for receiving the ultrasound signals transmitted from the ultrasound crystal secured to the locator catheter, a first ultrasound crystal beacon of said at least three ultrasound crystal beacons being located at the distal end of the reference catheter and being spaced apart from the remaining ultrasound crystal beacons, wherein the first ultrasound crystal beacon is adapted to be inserted into a vascular vessel; said ultrasound crystal beacons having coordinates that are pre-set with reference to an external location calibration system, and being able to emit and receive ultrasound signals; said external location calibration system for receiving signals from the crystal beacons and constantly calibrating the coordinates of the beacons on the reference catheter. The data acquisition computer is connected to the location calibration system for determining the location of the locator catheter.

The catheter system may further comprise a temperature sensor adjacent the electrode means, wherein the catheter system is equipped with a closed-loop temperature controller, and wherein the temperature sensor is adapted for providing temperature sensing signals to the closed-loop temperature controller for controlling the RF current delivery or other suitable energy delivery.

In order to provide increased torsional rigidity to the catheter shaft of the locator catheter or the reference catheter, the shaft material preferably comprises a polymeric tube having a Durometer in the range from 30D to 90D, usually from 40D to 65D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin or anti-thrombotic substrate on the surface of the catheter shaft. It is hypothesized that the coated heparin forms a barrier, while not releasing heparin from said surface, between the blood and the catheter surface to enhance biocompatibility during electrophysiology procedures.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

The catheter system of the present invention comprises a reference catheter serving as an emitter/receiver for ultrasound signals, a locator catheter serving as the mapping and/or ablation catheter which has the capability of emitting ultrasound signal, and a data acquisition computer. Both catheters have the capabilities of emitting and receiving ultrasound signals, which can be translated to digital data to be analyzed and stored by external data acquisition means.

The locator catheter is a standard electrophysiology catheter comprising an additional ultrasound crystal, which is made of piezoelectric materials. Said ultrasound crystal can vibrate at an ultrasonic frequency by giving a voltage impulse, or delivering an electric energy by receiving resonant ultrasound vibration. Thus, it can function as either a transmitter or a receiver. The data can be relayed to a data acquisition device for storage and analysis.

The reference catheter comprises a plurality of ultrasound crystals as "beacon". In one embodiment, the reference catheter comprises at least three ultrasound beacons which have pre-determined locations or three-dimensional coordinates with reference to an external locating calibration system. The crystals used in ultrasound imaging means can be shaped as a cylinder, a donut, a ring, a spiral, a mesh, or other appropriate shape. The crystals can be located on different apparatus or means to provide three-dimensional coordinates. The crystal is made of piezoelectric materials and has a conducting means to transmit the signal in either way for emitting and/or for receiving.

Figure 1:
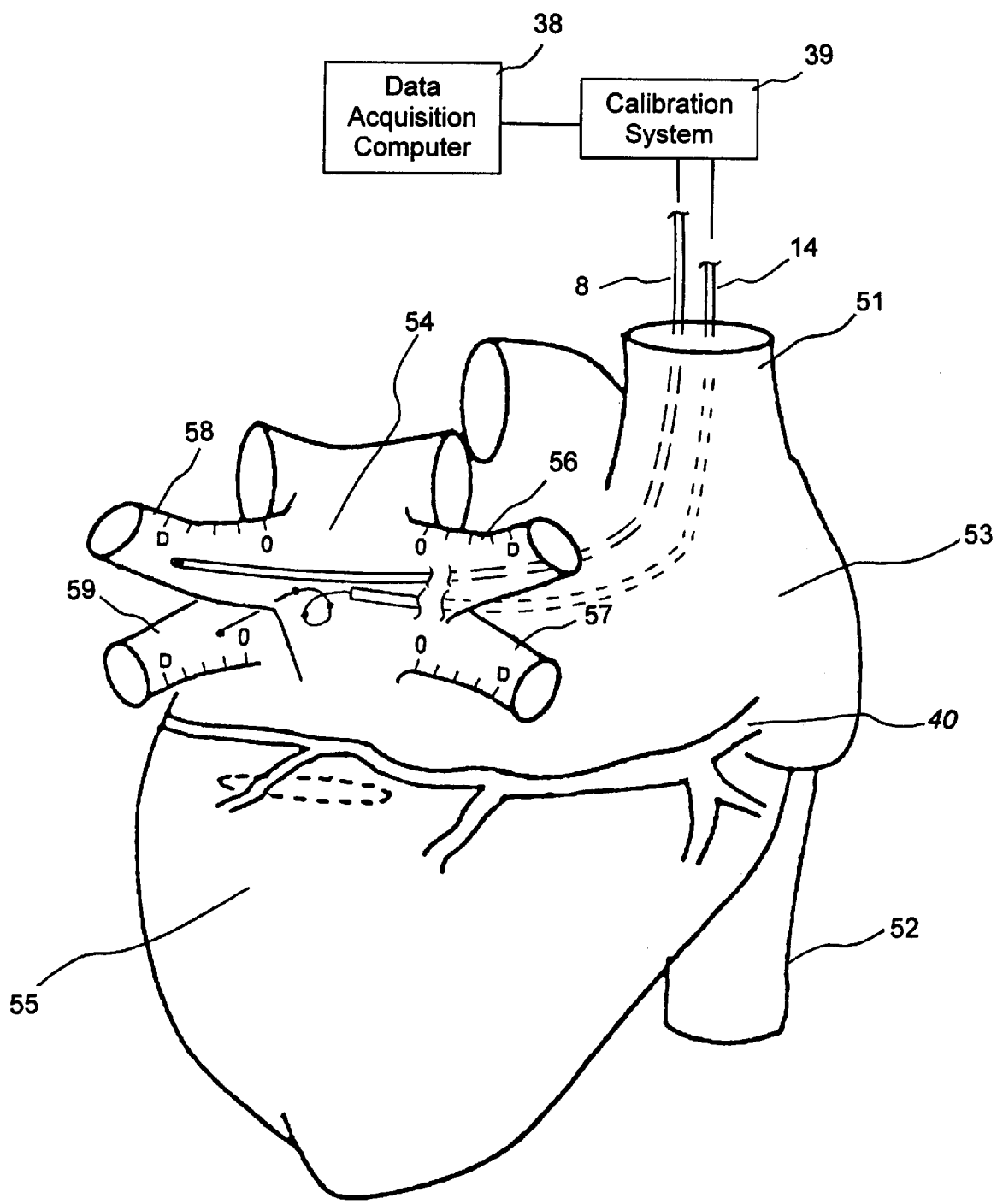
FIG. 1 is a perspective view of a catheter system having a locator catheter and a reference catheter under deployed state constructed in accordance with the principles of the present invention.

FIG. 1 shows a perspective view of the catheter system around a chamber of the heart and its adjacent pulmonary veins under deployed state. FIG. 1 shows a perspective view of the catheter system simulating an intravascular locating operation of the present invention. To better illustrate the application of the present invention, a human heart is shown in FIG. 1. Blood returning from superior vena cava 51 or inferior vena cava 52 flows back to the right atrium 53. A coronary sinus 40 is part of the coronary artery system to provide nutrient to the epicardial heart tissue, wherein the heart also comprises a left atrium 54, a left ventricle 55 and a right ventricle. A locator catheter 8 and a reference catheter 14 are shown passing through the superior vena cava 51 into the right atrium 53. Both catheters pass through the septal into the left atrium 54 for paroxysmal AFib treatment by using a standard trans-septal procedure. A normal people has four pulmonary veins: right superior pulmonary vein 56, right inferior pulmonary vein 57, left superior pulmonary vein 58, and left inferior pulmonary vein 59. In one example, a reference catheter 14 is inserted into the left atrium while its first ultrasound crystal beacon is inserted into the inferior pulmonary vein 59. After the distal portion of the reference catheter 14 is inside the vein 59, the reference catheter that has at least three ultrasound crystal beacons is used to setup the location system.

In this preferred embodiment. a reference catheter 14 comprises at least three ultrasound crystal beacons for receiving the ultrasound signals transmitted from the ultrasound crystal secured to the locator catheter 8, a first ultrasound crystal beacon of said at least three ultrasound crystal beacons being located at the distal end of the reference catheter and being spaced apart from the remaining ultrasound crystal beacons, wherein the first ultrasound crystal beacon is adapted to be inserted into a vascular vessel. Said ultrasound crystal beacons have coordinates that are pre-set with reference to an external location calibration system, and is able to emit and receive ultrasound signals. Said external location calibration system for receiving signals from the crystal beacons and constantly calibrating the coordinates of the beacons on the reference catheter.

Figure 2:
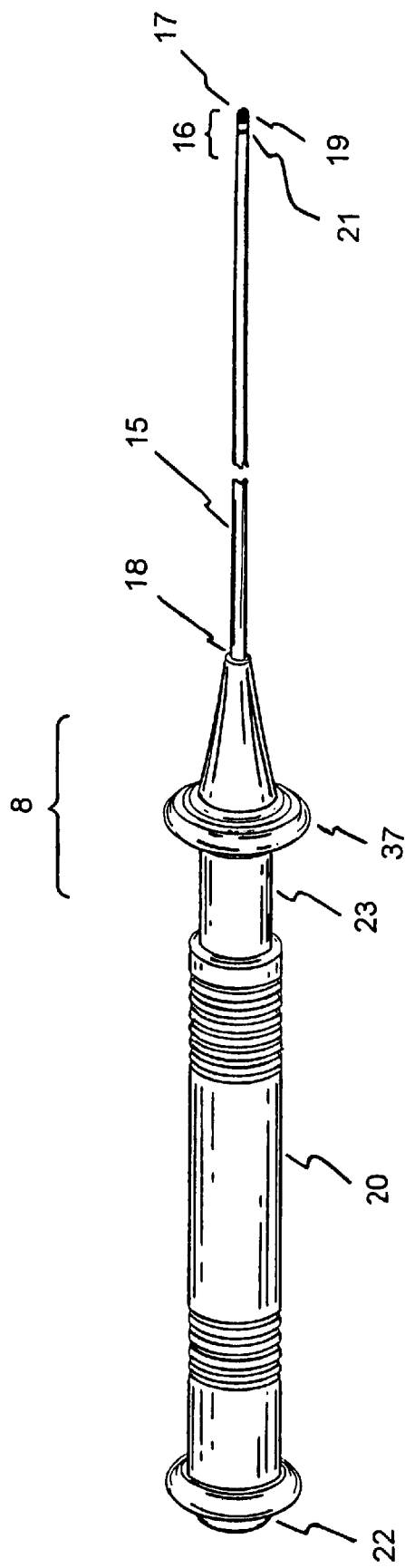
FIG. 2 is an overall view of the locator catheter having an ultrasound crystal at its tip section

FIG. 2 is an overall view of the locator catheter having an ultrasound crystal at its tip section. In one embodiment, a locator catheter 8 comprises a catheter shaft 15 having a distal tip section 16, a distal end 17, a proximal end 18 and at least one lumen extending therebetween, wherein at least one electrode 19 is secured at said distal tip section 16. A handle 20 is attached to the proximal end 18 of said catheter shaft 15. An ultrasound crystal 21 is secured on the catheter shaft proximal to the distal end 17. A connector 22 is usually attached to the proximal end of said handle 20. As a steerable catheter, a push-pull mechanism 23 is located on the handle. In another embodiment, the catheter comprises at least one temperature sensor and an external closed-loop temperature control means. In an alternate embodiment, the at least one electrode 19 can be a cylindrical tip electrode, a ring electrode, a spiral electrode, a mesh electrode, or the like.

The crystal 21 on the locator catheter 8 emits repeated signals at a pre-determined time period of fixed frequency, say e.g. at 20 kHz, to be received by the beacons of the reference catheter. The frequency can be changed to signify the sequence of the signals emission. The ultrasound waves, traveling at a constant speed, reach the at least three beacons at different time. Thus the distance between the crystal on the locator catheter and any beacon on the reference catheter can be calculated as $d_1 = v \times t_1$, where "$d_1$" is the distance between the crystal and the beacon no. 1, "v" is the known ultrasound velocity, and "$t_1$" is the traveling time of the ultrasound from the crystal to the beacon no. 1. The exact location of the tip of the locator catheter can be determined by the distances between it and the at least three of the beacons on the reference catheter, wherein the exact coordinates of the beacons on the reference catheter is pre-set or pre-determined with reference to an external location calibration means. In another embodiment, the locator catheter 8 comprises a plurality of ultrasound crystals to locate the whole tip section of said catheter.

The ultrasound frequency employed in this invention is selected from the range that its biological effects on the surrounding tissues or to the body of a patient are considered negligible and safe.

Figure 3:
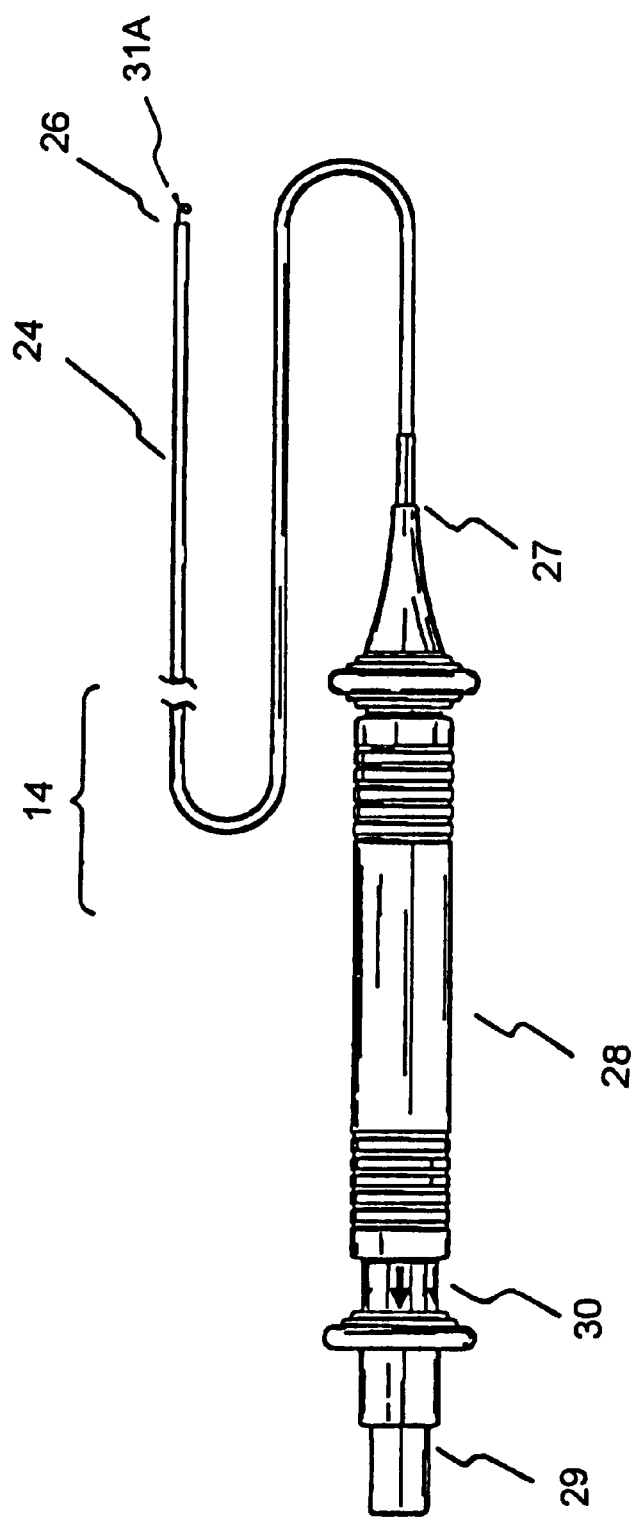
FIG. 3 is an overall view of the reference catheter under non-deployed state.

FIG. 3 is an overall view of a reference catheter under non-deployed state. The reference catheter 14 comprises a delivery shaft 24 and a spiral element 25 (shown on FIG. 4), wherein the spiral element stays within the delivery shaft under non-deployed state. The delivery shaft 24 having a distal end 26, a proximal end 27 and at least one lumen extending therebetween. A handle 28 is attached to the proximal end 27 of said delivery shaft 24. A connector 29 is usually secured to the proximal end of said handle 28. During catheter insertion into and removal from the body of a patient, the reference catheter 14 is under non-deployed state. After the reference catheter is advanced to the target ventricle or the atrium, the spiral element 25 is deployed. The deployment can be achieved by a pushing action at a push-pull mechanism 30 on the handle 28.

Figure 4:
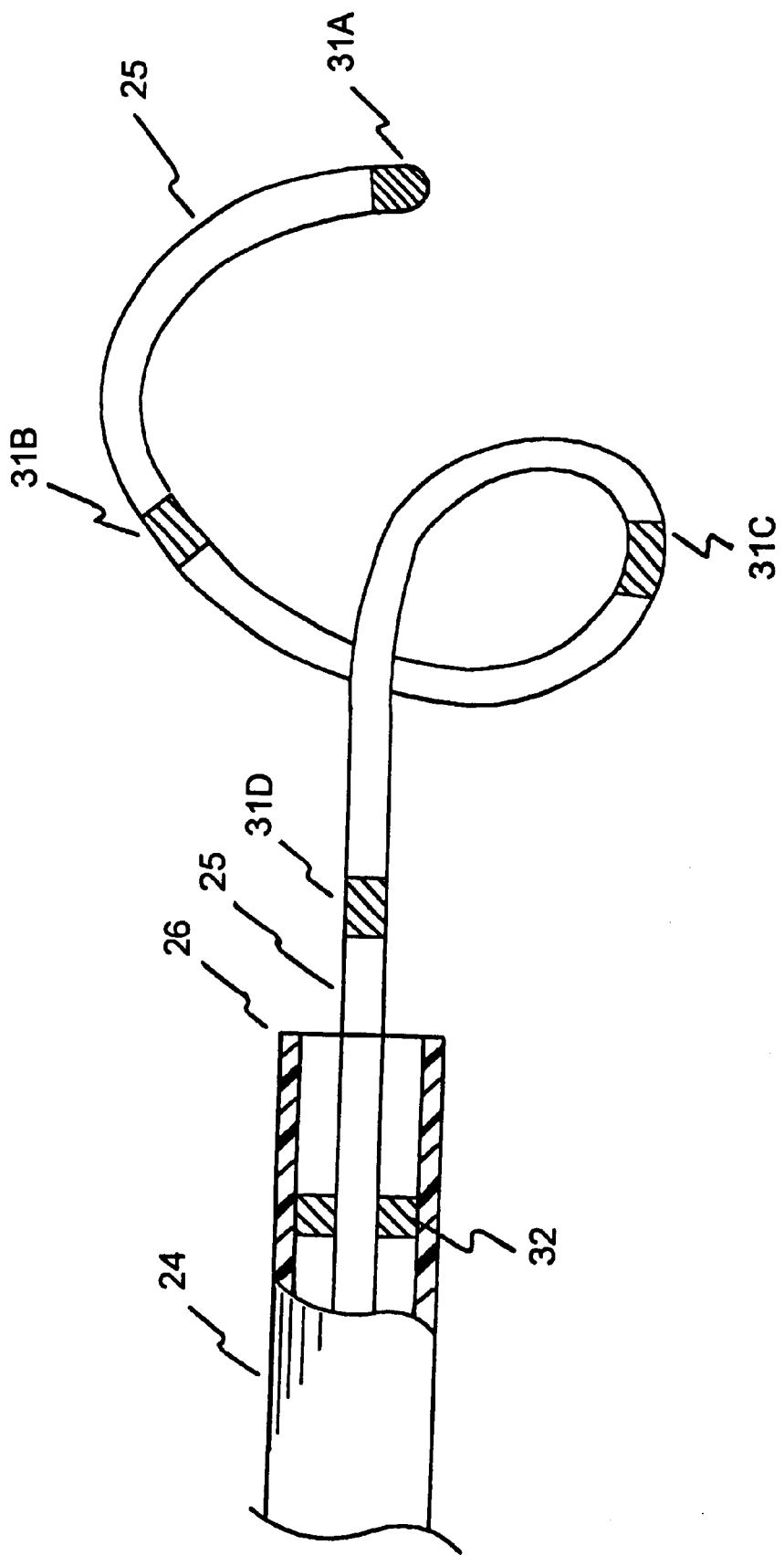
FIG. 4 is a close-up view of a preferred reference catheter under deployed state.

FIG. 4 shows the distal section of a preferred reference catheter under deployed state. The pre-shaped spiral element 25 comprises at least three crystal beacons 31A, 31B, 31C, and/or 31D that have the capability to emit and receive ultrasound signals. Their locations on the spiral element are preferably to form the three corners of a pyramid whereas the fourth corner is an ultrasound crystal on the locator catheter 8. In another preferred embodiment of the present invention, a first ultrasound crystal beacon 31A of said at least three ultrasound crystal beacons is located at the distal end of the reference catheter 14 and is spaced apart from the remaining ultrasound crystal beacons 31B, 31C, 31D, wherein the first ultrasound crystal beacon 31A is adapted to be inserted into a vascular vessel, such as a pulmonary vein. In another embodiment, said reference catheter 14 is designed as a spiral wire with crystals located strategically 120 degree apart in the case of three beacons system, or 90 degree apart in another case of four beacons system. A silicone type check valve 32 is installed at certain opening of the lumen of the catheter shaft 24.

Figure 5:
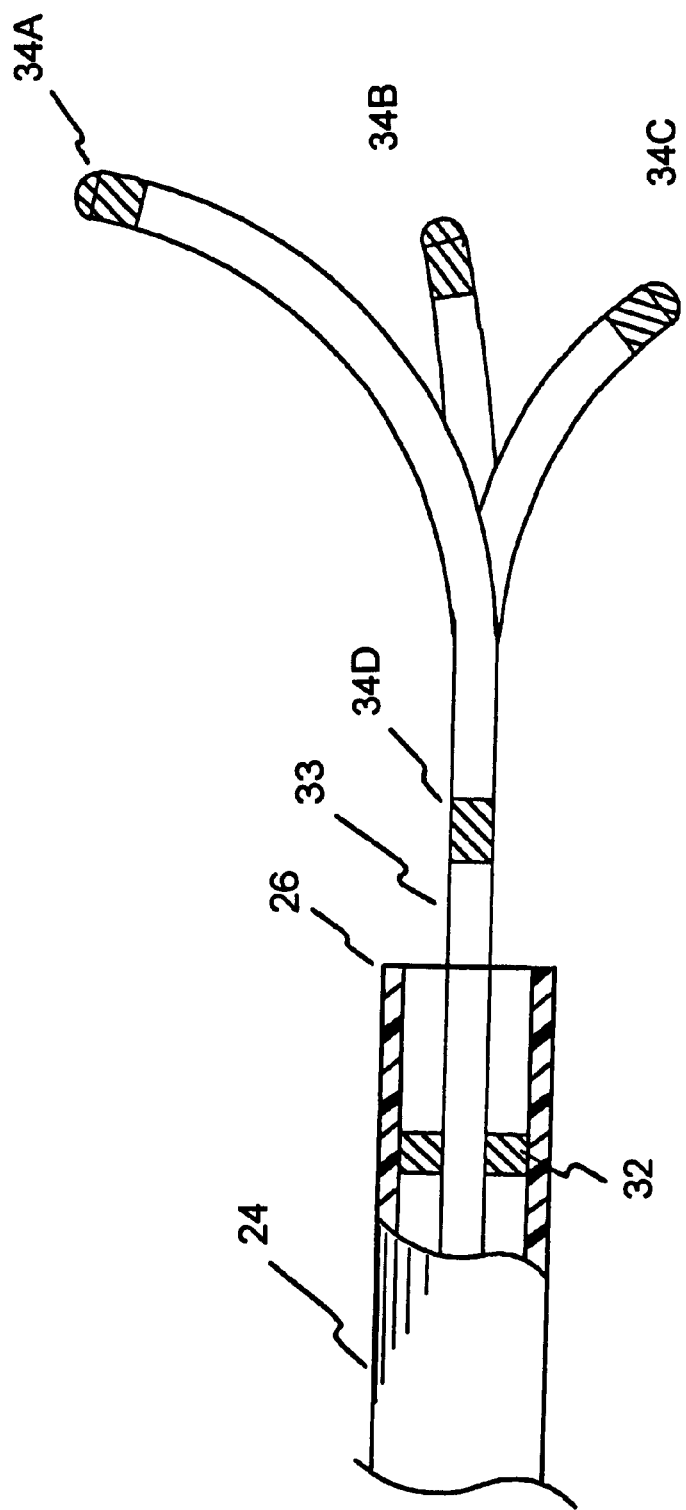
FIG. 5 is a close-up view of an alternate preferred reference catheter under deployed state.

FIG. 5 shows a close-up view of the distal section of an alternate preferred reference catheter under deployed state. The pre-shaped forky element 33 comprises at least three crystal beacons 34A, 34B, 34C, and/or 34D, which have the capability to emit and receive ultrasound signals. Similarly, a first ultrasound crystal beacon 34A of said at least three ultrasound crystal beacons is located by being spaced apart from the remaining ultrasound crystal beacons 34B, 34C, 34D, wherein the first ultrasound crystal beacon 34A is adapted to be inserted into a vascular vessel, such as a pulmonary vein.

After deployment, the multiple crystal beacons on the reference catheter are positioned either inside the body or outside the body of a patient. Their coordinates are calibrated frequently by emitting ultrasound signals from said beacons to be received by calibration system means 39 which is external of the body and is connected to the baseline data acquisition program in the data acquisition computer means 38. By constantly calibrating the coordinates of the beacons on the reference catheter, the received signals at the receiver beacons can be accurately correlated and input into said data acquisition computer to locate the locator catheter accurately and/or on a real-time basis.

In a further embodiment, the locator catheter 8 and the reference catheter 14 comprise a plurality of conducting wires that are disposed inside the lumen of the catheter shaft. The proximal end of said conducting wires is secured to a contact pin of the connector 22 or 29 that is secured at the proximal end of the handle 20 or 28. Therefrom, the conducting wires are connected to an external device or data acquisition means for analyzing the signal data from the ultrasound crystals.

The locator catheter 8 further comprises a steering mechanism at the handle for controlling the deflection of said distal tip section having at least one electrode and one ultrasound crystal. Usually a rotating ring or a push-pull plunger 37, such as the one shown in FIG. 2, is employed in the steering mechanism 23. In another embodiment, the steerable ablation catheter comprises a bidirectional deflection or multiple curve deflection of the tip section. One end of the steering wire is attached at certain point of the tip section of said catheter shaft. The other end is attached to the steering mechanism at the handle. The steering mechanism on a steerable catheter or device is well known to those who are skilled in the art. In another embodiment, the steering mechanism 23 at the handle 20 comprises means for providing a plurality of deflectable curves on the distal tip section 16 of the catheter shaft 15.

In an additional embodiment, the ablation version of the locator catheter of this invention further comprises a temperature sensing and closed-loop temperature control mechanism for the at least one electrode having a temperature sensor at about the tissue contact site of the electrode. The location of the temperature sensor is preferably in the very proximity of or inside the electrode. In a still further embodiment, a method for operating an ablation catheter further comprises a programmed temperature control mechanism for independently controlling the delivery of RF energy of each electrode of the ablation catheter.

In another particular embodiment, the material for the electrodes may consist of conductive metals such as platinum, iridium, gold, silver, stainless steel, Nitinol, or an alloy of their mixture.

A method for operating a catheter system having ultrasound locating capabilities comprises: (a) percutaneously introducing the reference catheter under non-deployed state through a blood vessel to the heart chamber; (b) deploying the catheter to position the at least three ultrasound crystal beacons, and placing the first ultrasound crystal beacon within a vascular vessel; (c) locating the at least three ultrasound crystal beacons in reference to an external calibration system; (d) constantly calibrating the location of the crystal beacons on the reference catheter; (e) percutaneously introducing the locator catheter through a blood vessel to the heart chamber; (f) deflecting the distal section of said locator catheter about a transverse axis to position the tip section; and (g) determining the coordinates of the locator catheter.

The catheter system of the present invention has several significant advantages over known catheters or electrophysiology techniques. In particular, the catheter system with intravascular ultrasound locating capability result in an effective electrophysiology procedure without undesired side effects of using a conventional x-ray imaging system.

From the foregoing, it should now be appreciated that an improved catheter system having an ultrasound locating capability has been disclosed for ablation and/or mapping electrophysiology procedures, including endocardial, epicardial, or body tissue and drug delivery operations for tumor or cancer management. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system for intravascular ultrasound location comprising:

a locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end for transmitting ultrasound signals; a connector secured to the proximal end of said handle;

a reference catheter comprising at least three ultrasound crystal beacons for receiving the ultrasound signals transmitted from the ultrasound crystal secured to the locator catheter, a first ultrasound crystal beacon of said at least three ultrasound crystal beacons being located at the distal end of the reference catheter and being spaced apart from the remaining ultrasound crystal beacons, wherein the first ultrasound crystal beacon is adapted to be inserted into a vascular vessel; said ultrasound crystal beacons having coordinates that are pre-set with reference to an external location calibration system, and being able to emit and receive ultrasound signals; said external location calibration system for receiving signals from the crystal beacons and constantly calibrating the coordinates of the beacons on the reference catheter; and a data acquisition computer connected to the location calibration system for determining the location of the locator catheter.

2. The catheter system of claim 1, wherein said ultrasound crystal beacons on the reference catheter are made of piezoelectric materials.

3. The catheter system of claim 2, wherein the shape of said ultrasound crystal beacons on the reference catheter is selected from the group consisting of a cylinder, a donut, a ring, a spiral, and a mesh.

4. The catheter system as in claim 1, further comprising a steering mechanism at the handle for controlling the steering of the distal tip section of said locator catheter.

5. The catheter system of claim 4, wherein said steering mechanism provides a plurality of deflectable curves on the distal tip section of said locator catheter.

6. The catheter system of claim 1, wherein the at least one electrode is selected from the group consisting of a cylindrical tip electrode, a ring electrode, a spiral electrode, and a mesh electrode. body of a patient.

7. The catheter system as in claim 6, further comprising the material of said electrode being selected from the group consisting of platinum, iridium, gold, silver, stainless steel, and Nitinol.

8. The catheter system as in claim 1, wherein said reference catheter is located inside the body of a patient, wherein said reference catheter comprises a delivery shaft having a distal end, a proximal end, and at least one lumen extending therebetween; a handle attached to the proximal end of said delivery shaft; a connector secured to the proximal end of said handle; and a spiral element being located within the delivery shaft under a non-deployed state.

9. The catheter system as in claim 1, further comprising a RF current generator, wherein RF current is delivered to the at least one electrode through an electrical conductor.

10. The catheter system as in claim 9, further comprising a temperature sensor near the at least one electrode, wherein the catheter system is equipped with a closed-loop temperature controller, and wherein the temperature sensor is adapted for providing temperature sensing signals to the closed-loop temperature controller for controlling the RF current delivery or other suitable energy delivery.

11. A method for operating a catheter system to locate the catheter system about a heart, the catheter system comprising a locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end; a connector secured to the proximal end of said handle; and a reference catheter comprising at least three ultrasound crystal beacons which have pre-determined locations with reference to an external locating calibration system, a first ultrasound crystal beacon of said at least three ultrasound crystal beacons being located at the distal end of the reference catheter and being spaced apart from the remaining ultrasound crystal beacons, wherein the first ultrasound crystal beacon is adapted to be inserted into a vascular vessel, wherein said ultrasound beacons can emit and receive ultrasound signals;

the method comprising the steps of:

(a) percutaneously introducing the reference catheter under non-deployed state through a blood vessel to the heart chamber;

(b) deploying the catheter to position the at least three ultrasound crystal beacons, and placing the first ultrasound crystal beacon within a vascular vessel;

(c) locating the at least three ultrasound crystal beacons in reference to an external calibration system;

(d) constantly calibrating the location of the crystal beacons on the reference catheter;

(e) percutaneously introducing the locator catheter through a blood vessel to the heart chamber;

(f) deflecting the distal section of said locator catheter about a transverse axis to position the tip section; and (g) determining the coordinates of the locator catheter.

12. The method for operating a catheter system to locate the catheter system about a heart as in claim 11, the catheter system further comprising a RF current generator, wherein radiofrequency current is delivered to a target tissue through the at least one electrode.

13. The method for operating a catheter system to locate the catheter system about a heart as in claim 11, wherein said ultrasound crystal beacons on the reference catheter are made of piezoelectric materials.

14. The method for operating a catheter system to locate the catheter system about a heart as in claim 11, wherein the shape of said ultrasound crystal beacons on the reference catheter is selected from the group consisting of a cylinder, a donut, a ring, a spiral, and a mesh.

15. The method for operating a catheter system to locate the catheter system about a heart as in claim 11, further comprising a steering mechanism at the handle of the locator catheter for controlling the steering of the distal tip section of said locator catheter.

16. The method for operating a catheter system to locate the catheter system about a heart as in claim 15, wherein said steering mechanism provides a plurality of deflectable curves on the distal tip section of said locator catheter.

17. The method for operating a catheter system to locate the catheter system about a heart as in claim 11, wherein the at least one electrode is selected from the group consisting of a cylindrical tip electrode, a ring electrode, a spiral electrode, and a mesh electrode.

18. The method for operating a catheter system to locate the catheter system about a heart as in claim 11, the catheter system further comprising a RF current generator, wherein RF current is delivered to the at least one electrode through an electrical conductor.

19. The method for operating a catheter system to locate the catheter system about a heart as in claim 18, the catheter system further comprising a temperature sensor near the at least one electrode, wherein the catheter system is equipped with a closed-loop temperature controller, and wherein the temperature sensor is adapted for providing temperature sensing signals to the closed-loop temperature controller for controlling the RF current delivery or other suitable energy delivery.

* * * * *